United States Patent [19]

Koenig

[11] 4,277,420

[45] Jul. 7, 1981

[54] EPHEDRINE AND PSEUDOEPHEDRINE PRECURSORS

[75] Inventor: Karl E. Koenig, Creve Coeur, Mo.

[73] Assignee: Monsanto Company, St. Louis, Mo.

[21] Appl. No.: 78,111

[22] Filed: Sep. 24, 1979

[51] Int. Cl.$^3$ .................... C07C 103/20; C07C 103/75
[52] U.S. Cl. ..................................... 560/24; 560/142; 560/32; 562/442; 562/451; 564/185; 564/219; 564/364; 564/381; 260/465 D
[58] Field of Search ............... 260/562 R, 465, 562 P, 260/562 A, 558 P; 560/24, 32

[56] References Cited

U.S. PATENT DOCUMENTS

| | | |
|---|---|---|
| 2,458,420 | 1/1949 | Reynolds et al. ............... 260/562 R |
| 2,458,422 | 1/1949 | Reynolds et al. ............... 260/562 R |
| 4,061,767 | 12/1977 | Ertel et al. ....................... 260/465 D |

*Primary Examiner*—Winston A. Douglas
*Assistant Examiner*—Raymond K. Covington
*Attorney, Agent, or Firm*—Joseph D. Kennedy; James W. Williams, Jr.

[57] ABSTRACT

Preparation of novel prochiral olefinic compounds which can be asymmetrically hydrogenated to enantiomers, which are converted to ephedrine and pseudoephedrine by described procedures.

21 Claims, No Drawings

EPHEDRINE AND PSEUDOEPHEDRINE PRECURSORS

This invention is concerned with olefinic precursors which are amenable to asymmetric reduction to form asymmetric compounds which can be converted to ephedrine and pseudoephedrine.

BACKGROUND OF THE INVENTION

Ephedrine and pseudoephedrine are medicinal compounds of known value in cold preparations and other medicinal uses. The compounds, which are diasteriomers have in the past been produced by procedures involving a resolution step to obtain the desired stereoisomer, which is always a laborious and expensive process because of the fractional crystallization and recycle loops necessary. It is also known that some olefins can be asymmetrically hydrogenated over rhodium and other metal coordination catalysts having optically active ligands.

SUMMARY OF THE INVENTION

The present invention involves a novel class of prochiral olefin compounds which can be used in effective manner for introduction of optical activity in novel routes for production of the optically active compounds ephedrine and pseudoephedrine. The compounds are characterized by the structure:

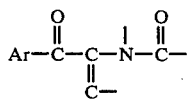

(in which Ar represents an aromatic group), and the olefinic bond therein can be asymmetrically reduced to provide compounds (in enantiomeric excess) which can be converted to ephedrine and pseudoephedrine and their derivatives and related compounds.

The invention also involves methods of preparing such compounds, and methods of preparing ephedrine and pseudoephedrine and related alkaloids utilizing such compounds. The invention avoids the need for the resolution step customarily employed to obtain ephedrine and pseudoephedrine in desired enantiomeric forms.

DETAILED DESCRIPTION OF THE INVENTION

Novel compounds of the present invention can be represented by the formula:

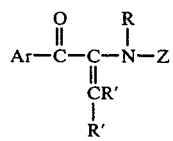

wherein

R and R' are selected from hydrogen, lower alkyl, and aryl, and

Z is selected from substituted or unsubstituted acyl, and Ar is an aromatic group, including substituted and unsubstituted phenyl groups bonded at a phenyl carbon atom to the adjacent carbonyl group.

A more proscribed group of the compounds of the present invention are represented by the formula:

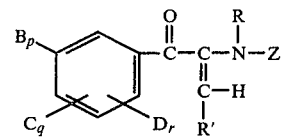

wherein

R, R' and Z are defined as above, and

B, C, and D are independently selected from hydrogen, alkyl, carboxyl, hydroxyl (and their metal salts), alkoxy, halogen, acyloxy, aryloxy, aralkoxy, amino, alkyl amino, nitro, cyano, and p, q, and r are integers from 0 to 5, provided that the sum of p, q and r equals 5. In the compounds, R will usually be hydrogen or lower alkyl, ordinarily hydrogen.

The acyl and substituted acyl variants used as Z can be such groups as acetyl, benzoyl, formyl, propionyl, butyryl, toluyl, nitrobenzoyl, etc. and groups composing urethano groups with the nitrogen, such as carbalkoxy groups, e.g. carbethoxy, etc., or other acyl variants commonly used as blocking groups in peptide synthesis. In general there is no advantage in utilizing large substituent groups, and ordinarily the substituent groups in the above formula, or other compounds herein, will not have more than 20 carbon atoms, and often less than 10, such as with lower alkyl groups, or hydrogen atoms. Novel compounds of the present invention can also be described as N(1-aroyl-1-alkenyl)amides.

A more specific class of compounds of the invention can be represented:

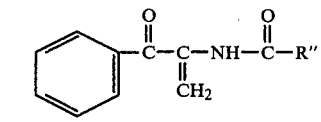

in which R" is selected from alkyl, aryl, alkoxy, or aryloxy, e.g. methyl, ethyl, hexyl, phenyl, tolyl, ethoxy, phenoxy, etc. Since the R" group will generally be removed or converted (along with the adjacent carbonyl) to a methyl group in preparing the desired ephedrine or other derivatives, there may be advantage in employing relatively simple groups such as methyl, ethoxy, etc. Many of the compounds of most interest for convenient use are N-acyl, 1-phenyl, 2-amino propenones.

The novel unsaturated compounds described herein are useful in that they are amenable to conversion to asymmetric compounds which can be further converted to useful optically active end products. The asymmetric reaction involved, illustrated with N-(1-benzoylethenyl)acetamide, is:

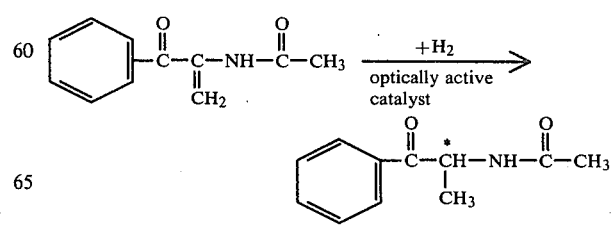

*shows the asymmetric carbon

It is fortuitous that this hydrogenation goes well and in asymmetric manner to produce the indicated acetamide with high enantiomeric excess of one isomer. The enantiomeric product can then be further reacted to reduce the benzoyl carbonyl to hydroxyl, and to hydrolyze the N-acyl group and replace it with a methyl, or reduce the N-acyl group directly to a methyl amine, to obtain ephedrine and pseudoephedrine:

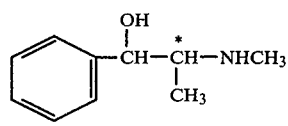

The conversions can involve a combination of reducing, methylation and acid or base treatment steps, as will be described further herein. By conducting the reduction of the carbonyl to hydroxyl with suitable catalyst, the reduction can be made asymmetric at the hydroxyl carbon to direct the reaction to either ephedrine, or its diasteriomer, pseudoephedrine. However, both isomers have medicinal activity and a mixture thereof is useful, and retains the stereoisometry at the α-(methylsubstituted) carbon atom, regardless of whether the reduction of the carbonyl is asymmetric. Ephedrine and pseudoephedrine are diasteriomers, but not enantiomers, and interconversion from one to the other is possible. See E. Schmidt, Arch. Pharm. 242, 380; 244, 239.

Thus a mixture of the diasteriomers is useful in itself or as a source of either isomer.

The compounds of the present invention can be conveniently asymmetrically hydrogenated, generally in high enantiomorphic excess, utilizing catalysts which have been found suitable for asymmetric hydrogenation. While such catalysts have been utilized with various types of olefinic compounds, it is not believed that they have been utilized heretofore for olefins having benzoyl and acyloamido substitutents on the same carbon atom, and the benzoyl group might be expected to produce a different effect than, for example, the carboxy group present in precursors in L-DOPA synthesis. These particular olefin compounds are not natural choices for synthesis as epehedrine precursors, as dl ephedrine can be readily produced in relatively simple reactions, without any need for production and hydrogenation of olefins. For example, ephedrine is produced by catalytic reduction of phenyl-methyl-diketone in the presence of methyl amine. However, such synthesis is not asymmetric, and it is necessary to have a resolution step to obtain R and S forms of ephedrine. By the present invention such forms can be obtained without resolution step, although methods for enantiomeric enrichment can be employed if desired for higher optical purity.

The novel olefinic compounds of the present invention can also serve as intermediates for the production of optically active amphetamines. Thus the compounds can be reduced with optically active catalysts, as in the ephedrine synthesis, to form an optically active N-acyl-2-aminopropiophenone, which is then subjected to further reaction:

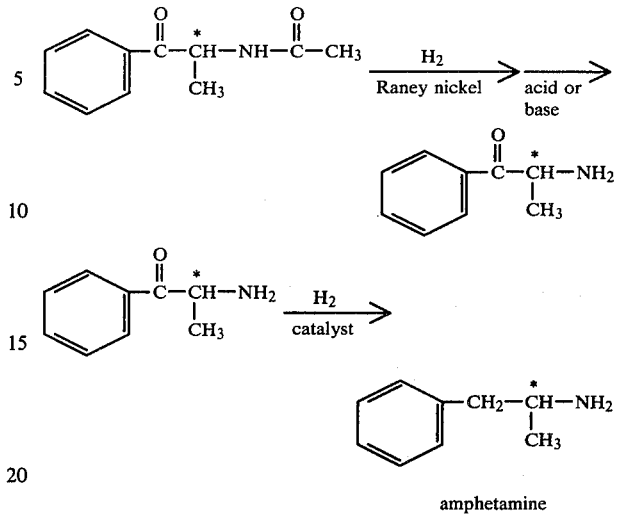

amphetamine

Either stereoisomer of amphetamine can be formed, depending upon the stereoisomeric form of the catalyst utilized to obtain the optically active N(1-benzoylethyl)acetamide.

The N(1-aroylvinyl)amide compounds of the present invention can be prepared by a number of routes from different starting reactants. Thus the compounds can be prepared by dehydrogenation of the corresponding N-acyl-2-aminopropiophenone by reaction with hypochlorite followed by base:

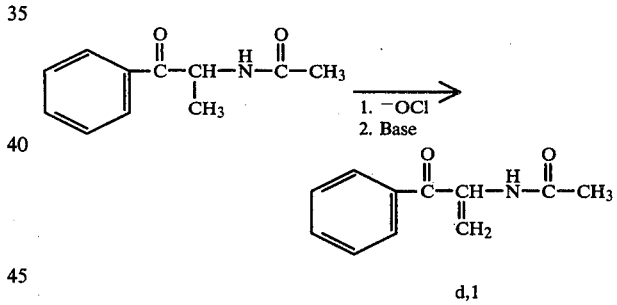

d,l

The N(1-benzoylvinyl)acetamide can then be asymmetrically hydrogenated to obtain the desired isomer of the N-acetyl-2-aminopropiophenone. Other aroylvinyl acetamides can be made by the same procedure which in effect is a dehydrogenation. For example, α-aminopropionic acid can be reacted with benzoic acid anhydride and base to obtain a racemic mixture of N-benzoyl 2-aminopropiophenone, which can then be chlorinated and dehydrochlorinated to effect dehydrogenation to N(1-benzoylvinyl)benzamide. This compound can then be asymmetrically hydrogenated to obtain an optically active form of N-benzoyl 2-aminopropiophenone, which in turn, can be converted to optically active ephedrine and pseudoephedrine by procedures described herein.

The olefinic compounds of the present invention can also be produced by reacting 1-aryl-1,2-alkane diones with an acylamide with mild heating, as by heating to reflux in benzene or toluene with a trace of acid:

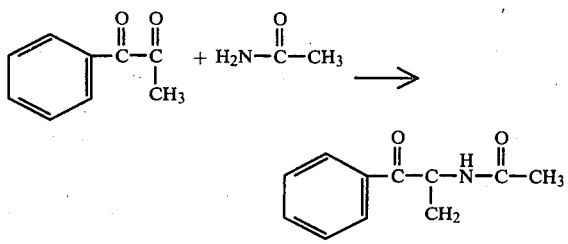

A similar reaction of phenyl-1,2-propanedione with alkyl carbamate produces N-(1-benzoylvinyl) alkyl carbamate

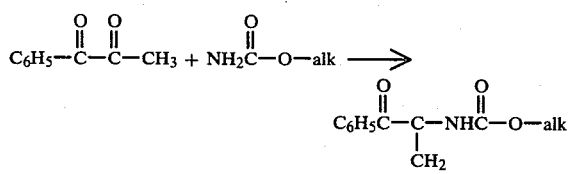

The carbamate can then be asymmetrically hydrogenated to obtain an optically active N(1-benzoylethyl) alkyl carbamate. The carbamate can then be reduced to convert the carbonyl group to hydroxyl, and the carbalkoxy group to methyl, employing LiAlH$_4$, NaBH$_4$ or other agents capable of effecting such reduction, thereby obtaining ephedrine and pseudoephedrine.

The compounds of the present invention can also be produced from oximes, as by converting aryldiketones to the appropriate oxime and reacting with acid anhydrides:

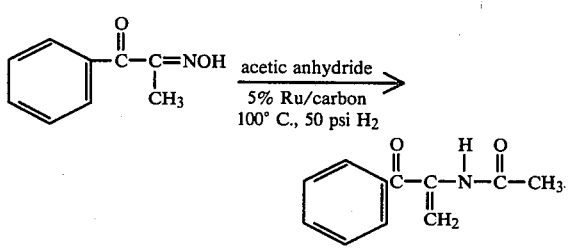

See Motoo Hazama, German Pat. No. 27 18 552 (1977) for the reaction with anhydride.

A similar reaction, but utilizing palladium on carbon as the catalyst, produces N-acetyl-2-aminopropiophenone which can then be converted to N(1-benzoylethenyl) acetamide by treatment with sodium hydrochlorite followed by base.

The oximes for use in the preparations herein can be readily prepared by reaction of nitrites with the corresponding diketone, e.g. α-keto-propiophenone is converted to 1-phenyl-2-oxime-1,2-propane-dione by reaction with butyl nitrite. Thus the same diketones can be utilized in the oxime route as are employed in some of the other procedures described herein for preparing the compounds of the present invention.

In hydrogenating the compounds of the present invention, any catalysts effective for asymmetric hydrogenation of olefins can generally be used, such as metal coordination complex catalysts containing optically active ligands, although some will give better results than others.

The optically active ligands on the catalysts can generally be selected so as to produce the desired enantiomer. Cobalt, rhodium, iridium and ruthenium coordination complexes are among the most prominent catalysts utilized for this type of synthesis and will generally be employed with the present compounds, especially rhodium catalysts. For example, catalysts described in U.S. Pat. Nos. 3,849,480 and 4,008,281 can be employed, and the disclosure of those patents is incorporated herein by reference. A class of suitable catalysts can be represented by $$MX_nL_3$$

wherein M is a suitable metal, X is halogen or hydrogen, and L is a ligand, such as a phosphine or arsine and n is one or three. Trisorganophosphorus or trisorganoarsenic are suitable ligands, and at least one ligand is optically active to provide the asymmetric synthesis. The olefinic group in the compounds hydrogenates with the catalysts more readily than the adjacent carbonyl. Under stringent conditions, the carbonyl will hydrogenate, but it is preferable to leave this reduction for a separate step. The carbonyl reduction tends to be less asymmetric, and reduction at this site has an undesirable effect upon the olefin hydrogenation, generally making it less asymmetric. The hydrogenation will generally be carried out under mild conditions, at relatively low hydrogen pressure and relatively mild temperatures, such as elevated pressures up to 100 psi H$_2$ and temperatures up to 100° C. or so. For both ephedrine and pseudoephedrine, the S enantiomer is necessary with regard to the asymmetric center at the nitrogen substituted carbon. Whether S enantiomers are produced by use of the S or R catalytic ligand depends upon the particular ligand.

As discussed, the compounds of the present invention can be asymmetrically hydrogenated to N(1-aroylethyl) amides which are optically active. The amides can then readily be converted by various routes to ephedrine and pseudoephedrine, retaining the optical activity, the conversion being summarized:

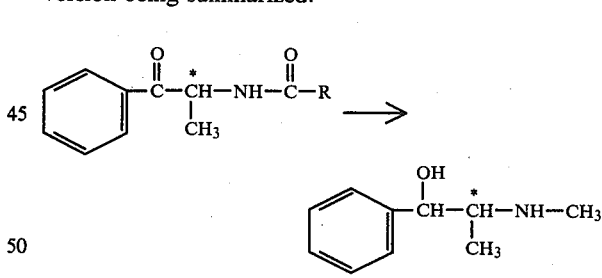

where R can be such groups as alkyl, phenyl, etc. The illustrated conversion of carbonyl to hydroxyl can be effected by various agents capable of reducing a carbonyl group to hydroxyl, e.g. hydrogen over Raney nickel or other hydrogenation catalyst, sodium borohydride, lithium aluminum hydride, etc. The acyl group on the nitrogen is removed by hydrolysis, generally by acid or base catalysis. The methyl group on the nitrogen in the ephedrine product is supplied by methylating with a methylating agent, e.g. dimethyl sulfate in the presence of base, or with methyl chloride or other methylating agents. The order of the reactions can be varied, as 1. reduction, 2. hydrolysis, 3. methylation; or 1. methylation, 2. reduction, 3. hydrolysis; or 1. reduction, 2. methylation, 3. hydrolysis. The various partial conversion compounds are produced as intermediates and can be isolated, if desired, but there ordinarily is no reason for doing so. As described hereinbefore, when the group on the nitrogen is carbalkoxy (R is alkoxy), it is not necessary to methylate or hydrolyze as the carbalkoxy group can be reduced to a methyl group, and the carbonyl group can be reduced to hydroxyl, employing the same agent. A mixture of NaBH₄ and AlCl₃ has been found particularly effective for this reduction. The mixture may have interacted to form AlH₃ as the actual agent which carries out the reaction. The stated mixture is considered effective for the reduction of urethane groups in general. Mixtures of AlCl₃ with aluminum metal, or aluminum sesquichlorides, or other aluminum halides can, if desired, be substituted for the AlCl₃ with at least some of the desired reducing properties being obtained.

In the illustrative preparations herein to prepare compounds represented by:

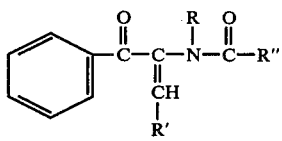

and convert them to further derivatives, simple groups as substituents are ordinarily used. However other groups can be used. Thus the phenyl group can generally be replaced in the reactions by phenyl groups with substituents of the type discussed herein so long as they do not unduly interfere. The methyl group in diketone or other reactants can be replaced by other alkyl, aryl or other groups to produce the R' groups in the formulas of compounds set forth herein. While some of the illustrated reactions necessarily lead to compounds in which the R substituent on the nitrogen is hydrogen, it is possible to methylate or alkylate the nitrogen; or in some cases it may be feasible to use N-alkyl amides or amino acids in the preparations. It may be convenient to have a methyl substituent on the nitrogen, as ephedrine has such a group and this permits further variation in the conversion to ephedrine. The R" group can be varied from varous alkyl to aryl groups by appropriate choice of acid anhydride and compounds suitable for reaction therewith. In general in the preparations, methyl can be replaced by other alkyl groups. Compounds in which the R" group is H, are not generally amenable to preparation by the described procedures, although such compounds have an advantage in that the

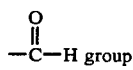

can be reduced to form the N-methyl group of ephedrine and related compounds.

The compounds and processes of the present invention are useful in the preparation of ephedrine and related alkaloids having useful pharmacological properties. Ephedrine and pseudoephedrine are used in cold preparations, and have been used in treatment of asthma and for other purposes. Amphetamines have been used for stimulatory effects and related purposes. The novel classes of compounds illustrated herein can be expected to lead to compounds of similar useful properties upon conversion by the procedures described herein. In some cases the varying substituent groups can be converted to, or replaced by, the groups present in ephedrine. In others, such as where methyl is replaced by other alkyl or phenyl, or phenyl by substituted phenyl, the ephedrine derivative produced can be expected to have properties in common with ephedrine. The described substituents in the novel classes of compounds described herein are not expected to interfere unduly with the described asymmetric character of the hydrogenation of the olefin group in the compounds; therefore the compounds can be utilized in preparing various ephedrine and related derivatives in enantiomeric form.

The following examples illustrate preparation and use of some of the compounds of the present invention and their precursor compounds. Various other described compounds can be readily prepared by these or various other procedures described herein.

EXAMPLE 1

Preparation of 1-phenyl-2-oxime-1,2-propanedione

The following procedure is essentially as reported in the literature; Org. Syn., II, 363.

Propiophenone (14.6 g. 0.1 mol) was diluted with 100 ml anhydrous diethyl ether in a nitrogen purged 200 ml 3-necked round bottom flask which was equipped with a magnetic stirring bar, addition funnel and syringe septum. While HCl gas was bubbled through the solution, butyl nitrite (10.3 g, 0.1 mol) in 10 ml of anhydrous diethyl ether was added dropwise at such a rate as to create a gentle reflux. Addition time was approximately forty minutes. After ten additional minutes of HCl addition, the gas was turned off and the solution was stirred at room temperature for forty-eight hours. The solvent was removed under reduced pressure and the residue recrystallized from 46 ml of toluene at $-3°$ C. After drying the resulting crystals at 80° C. for 1½ hours, 9.02 g (52% yield) of 1-phenyl-2-oxime-1,2-propanedione was obtained (mp=113°–114° C., very sharp).

EXAMPLE 2

Preparation of N-(1-Benzoylvinyl)acetamide

In a glass 90 ml hydrogenation bottle equipped with a magnetic stirring bar was placed 1.0008 g (6.15 mmols) of 1-phenyl-2-oxime-1,2-propanedione, 0.12 g of 5% ruthenium on carbon and 26 ml of acetic anhydride. The solution was purged with nitrogen and pressurized to 50 psi with hydrogen. After heating to 50° C., the solution was stirred at temperature for forty-eight hours. The pressure was released and the solvent removed under reduced pressure (1 mm/65° C.). The resulting oil was purified on a dry silica gel column (½"×12") using CH₂Cl₂ as the eluant. The column was followed by thin layer chromatography and the fastest moving band collected 0.63 g(63% yield) of N-(1-benzoylvinyl) acetamide (mp=73°–79° C.).

EXAMPLE 3

Preparation of N-(α-methylphenacyl)acetamide

In a 50 ml glass hydrogenation bottle equipped with a magnetic stirring bar was placed 0.7496 g (3.97 mmol) of N(1-benzoylvinyl)-acetamide in 20 ml of 100% ethanol. Nitrogen gas was bubbled through for ten minutes. Cyclooctadiene-1,5[(R,R)-1,2-ethanediylbis(o-methoxyphenyl)-phenylphosphine] rhodium tetrafluoroborate (7.4 mg. 0.01 mmol) was added and the bottle was evacuated and filled with 30 psi of nitrogen five times. The solution was heated to 50° C. and 50 psi of hydrogen was applied. After one hour, hydrogen uptake ceased. The pressure was released and the solution was diluted to 50 ml with 100% ethanol at 20° C.-$[\alpha]_D^{20} = -59.5°$. The solvent was removed at reduced pressure (1 mm 150° C.) and a chiral shift study with tris [3-(heptafluoropropylhydroxymethyene)d-camphorate] europium III was conducted. The study indicated an 85% enantiomeric excess of (S)N-($\alpha$-methylphenacyl)acetamide.

EXAMPLE 4

Synthesis of N-(1-benzoylvinyl)acetamide

In a flame dried, nitrogen purged 100 ml round bottom flask equipped with a magnetic stirring bar and a reflux condenser were placed 0.5 g (3.38 mmol) $\alpha$-ketopropiophenone, 0.2 g (3.39 mmol) acetamide, 30 mg paratoluenesulfonic acid, 10 mg hydroquinone and 30 ml toluene. The mixture was refluxed under nitrogen for twenty hours. The solution was then cooled to room temperature and the solvent was removed under reduced pressure giving a mixture of aryl containing products which were 51% $\alpha$-ketopropiophenone, 47% N-(1-benzoylvinyl) acetamide (based on nmr integration).

EXAMPLE 5

Synthesis of dl N-($\alpha$-methylphenacyl)benzamide

In a flame dried nitrogen purged 100 ml round bottom flask equipped with a nitrogen inlet, magnetic stirring bar and reflux condenser were placed 12 ml (152 mmol)pyridine, 34 g (150 mmol)benzoic anhydride and 3 g (34 mmol) d,l-alanine. The solution was heated at 125°-25° C. for two hours. After cooling to room temperature, the solution was carefully diluted with saturated sodium bicarbonate and the product taken up in ethyl acetate. The organic layer was separated and was washed ten times (100 ml water each). The solvent was removed under reduced pressure. This material was steam distilled for 1½ hours and the pot residue taken up in ethyl acetate and carefully washed with sodium bicarbonate (3×100 ml). The solution was filtered through a 1"×3" plug of dry silica gel and the solvent removed under reduced pressure. The resulting oil was crystallized from diethylether by slow evaporation to pure dl N-($\alpha$-methylphenacyl) benzamide, mp=87°-89° C.

EXAMPLE 6

Synthesis of N-(1-benzoylvinyl)benzamide

In a flame dried nitrogen purged 50 ml round bottom flask equipped with a magnetic bar, nitrogen inlet and septum were placed 0.83 g (3.28 mmol) N-($\alpha$-methylphenacyl) benzamide (prepared as in Example 5) and 10 ml of methanol. Sodium tetraborate (0.14 g, 0.37 mmol) was added. After five minutes the solution was homogeneous and 0.56 ml (4.98) of freshly prepared t-butylhypochlorite was added. After approximately one hour the solvent was removed under reduced pressure to give a light oil which was placed on a ½"×10" dry silica gel column using methylene chloride as the eluant giving 0.63 g ($R_f$=0.53 with CHCl$_3$) of N-($\alpha$-methylphenacyl)-N-chlorobenzamide. This material was taken up in carbon tetrachloride and 0.4 g of DABCO amine was added in one portion at room temperature. After ten minutes the solution was filtered giving virtually pure N-(1-benzoylvinyl) benzamide ($R_f$=0.47 in CHCl$_3$) in quantitative yield (light yellow oil).

DABCO amine is 1,4-diazabicyclo (2.2.2.) octane, also called triethylenediamine. Amines in general or other bases can also be employed to effect the dehydrohalogenation. The combination of sodium tetraborate and t-butylhypochlorite is convenient for laboratory use, but other forms of sodium hypochlorite, or hypochlorite and base, can be used.

EXAMPLE 7

Synthesis of ethyl N-(1-benzoylvinyl)carbamate

In a flame dried nitrogen purged 100 ml round bottom flask equipped with a magnetic stirring bar, Dean-Stark trap and a reflux condenser were added 3.0 g (20.3 mmol) $\alpha$-keto-propiophenone, 3.6 g (40.5 mmol) urethane (ethyl carbamate),10 mg (0.1 mmol) hydroquinone, 60 mg (0.3 mmol) paratoluenesulfonic acid and 20 ml of toluene. The mixture was refluxed under nitrogen with vigorous stirring for 3½ hours. The solvent was removed under reduced pressure and the residue distilled through a short path distillation column giving approximately 1 g of ethyl N-(1-benzoylvinyl)carbamate bp$\approx$130°-135° C. (1 mm).

The hydroquinone in the above Example was employed as a polymerization inhibitor, but its use is not necessary.

EXAMPLE 8

Synthesis of ethyl-N-($\alpha$-methylphenacyl)carbamate

In a 60 ml glass pressure bottle equipped with a magnetic stirrer were placed 25 ml of 100% ethanol, 0.3511 g of a mixture which was composed of 80%-N-(1-benzoylvinyl)urethane, 10% urethane and 9% $\alpha$-ketopropiophenone, and 9×10$^{-3}$ g of cyclooctadiene-1,5 [(R,R)-1,2-ethanediylbis(o-methoxyphenyl)phenyl phosphine] rhodium tetrafluoroborate. The solution was heated to 50° C.; purged by filling the reactor with nitrogen followed by evacuation. This sequence was conducted five times. The pressure bottle was pressurized to 50 psi with hydrogen and the reaction monitored until hydrogen uptake ceased (approximately two hours). The pressure was released and the solent was removed under reduced pressure at 50° C. The residue was purified on dry silica gel column using chloroform as the eluant. The column was followed by thin layer chromatography and the band with $R_f$=0.24 collected giving over 200 mg of N-($\alpha$-methylphenacyl)urethane, $[\alpha]_D^{20}$=20.3 (C,1,4 ethanol). This, in the context of other results, indicates a large excess of the S form. At times it may be convenient to employ a mixture as described above containing the N(1-benzoylvinyl)urethane reactant, obtainable in procedures like that of Example 7, rather than the pure compound.

EXAMPLE 9

Synthesis of Ethyl N-(2-hydroxyl-1-methyl-2-phenylethyl)carbamate

In a flame dried, nitrogen purged 10 ml round bottom flask equipped with a nitrogen inlet and a magnetic stirring bar were placed 60.3 mg (0.273 mmol) of optically active ethyl N-($\alpha$-methylphenacyl)carbamate obtainable in procedures like Example 8, and 3 ml of 100% ethanol. Sodiumborohydride (24 mg, 1.6 mmol) was added at room temperature in one portion. The mixture was stirred at room temperature for one hour. The solvent was then removed under reduced pressure (1 mm, 40° C.) yielding a residue which was taken up in deuteriochloroform and filtered. By nmr the starting material had been fully reduced to give approximately a 70/30; erythro/threo mixture of ethyl-N-(2-hydroxyl-1-methyl-2-phenylethyl) carbamate, with the S form (at the 2-carbon) being in large excess. The S form could be obtained in approximately 100% excess if the starting -methylphenacyl carbamate were converted to about 100% S form by crystallization. Alternatively, the product of the present example can be purified by crystallization to obtain the desired excess of S form. A small amount of ethanol was still present which was removed as an azeotrope with nitromethane.

EXAMPLE 10

Synthesis of 2(methylamino)-1-phenyl propanol

In a flame dried nitrogen purged 5 ml round bottom flask equipped with a magnetic stirring bar and a nitrogen inlet were placed 50 mg (0.22 mmol) of ethyl-N-(2-hydroxy-1-methyl-2-phenylethyl) carbamate (as prepared in Example 9) and 3 ml of anhydrous diethyl ether. Lithium aluminum hydride (LAH) was added (10 mg. 2.6 mmol) in one portion. The suspension was stirred for 2¼ hours at room temperature. The reaction was quenched with water (carefully) and the products extracted with diethylether. The reaction had gone 9% to completion. The mixture was taken up in 5 ml tetrahydrofuran (THF). LAH (30 mg, 7.8 mmol) was added and the mixture refluxed for fifteen minutes. The reaction was carefully quenched with water and extracted with diethylether. The rection had gone 40% to completion by nmr. The material was then refluxed in 5 ml of THF with 30 mg LAH for an additional 1¼ hours. The mixture was cooled, quenched with water and extracted with diethylether giving cleanly 80% of 2-(methylamino)-phenylpropanol. The material was purified by acid extraction with HCL/water, neutralization and back extraction with diethylether. With the starting carbamate being largely in the S form (at the α-carbon), the product is mainly a mixture of ephedrine and pseudoephedrine.

What is claimed is:

1. As new compounds, the compounds represented by:

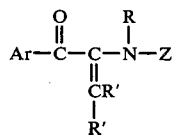

in which Ar represents substituted or unsubstituted phenyl. each R and R' are independently selected from hydrogen, lower alkyl and aryl, and Z is selected from substituted or unsubstituted acyl.

2. As new compounds the class of N(1-aroyl-1-alkenyl) amides.

3. As new compounds, the compounds of claim 2 further defined as N(1-aroyl-1-alkenyl)acetamides.

4. As new compounds, the compounds of claim 2 further defined as N(1-benzoyl-1-alkenyl)acetamides.

5. A compound of claim 2 which is N(1-benzoyl-ethenyl)acetamide.

6. A compound of claim 2 which is N(1-benzoyl-1-ethenyl)benzamide.

7. As new compounds, the class of N(1-aroyl-1-alkenyl)carbamates.

8. The compounds of claim 7 further defined as N-(1-benzoyl-1-alkenyl) alkyl carbamates.

9. A compound of claim 7 which is N(1-benzoyl-1-ethenyl) ethyl carbamate.

10. As new compounds, the compounds represented by:

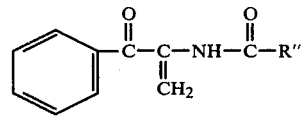

in which R" is selected from alkyl, aryl, alkoxy or aryloxy.

11. The method of obtaining optical enantiomers of compounds represented by the structure:

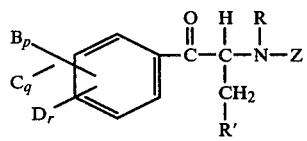

wherein R, R' and Z are defined as in claim 1 and B, C, and D are independently selected from hydrogen, alkyl, carboxyl, hydroxyl, alkoxy, halogen, acyloxy, aryloxy, aralkoxy, amino, alkyl amino, nitro, and cyano, and p, q, and r are integers from 0 to 5, provided that the sum of p, q and r equals 5, which comprises asymmetrically hydrogenating the compounds of claim 1 over an asymmetric hydrogenation catalyst.

12. The method of claim 11 in which a metal coordination complex with an optically active ligand is employed as the catalyst.

13. The method of claim 11 in which the catalyst is a coordination metal complex capable of homogeneously catalyzing the hydrogenation of an olefin comprising a metal selected from rhodium, iridium, ruthenium and cobalt and an arsine or phosphine ligand wherein at least one arsine or phosphine ligand is optically active.

14. The method of claim 11 in which the metal is rhodium.

15. The method of obtaining optical enantiomers of compounds represented by:

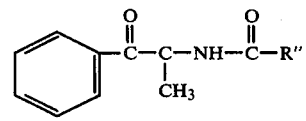

in which R" is selected from alkyl, aryl, alkoxy or aryloxy, which comprises asymmetrically hydrogenating the compounds of claim 10 with the use of an asymmetric hydrogenation catalyst.

16. The method of producing N(1-aroylethenyl) carbamates by reaction of a 1-aryl-1,2-diones with a carbamate.

17. The method of producing one enantiomer of an N-(1-aroylethyl) carbamate in excess which comprises reacting a 1-aryl-1,2-dioene with an ester of carbamic acid to produce N(1-aroylethenyl) carbamate ester, and then hydrogenating over an asymmetric hydrogenation catalyst to obtain an optically active N-(1-aroylethyl) carbamate.

18. The method of producing aryl(1-methylamino alkyl) carbinols with optical structures of ephedrine and pseudoephedrine which comprises reacting 1-aryl-1,2-dione with a carbamate to obtain an N-(aroylethenyl) carbamate, then hydrogenating with hydrogen and an asymmetric hydrogenation catalyst to obtain an S enantiomorph of N-(1-aroylethyl) carbamate, then reducing with a reducing agent to convert the urethane group of the carbamate to a methyl group and the carbonyl group to a hydroxyl, producing an aryl (1-methylaminoalkyl) carbinol with a mixture of optical configurations of ephedrine and pseudoephedrine.

19. The method of claim 18 in which N-aroylethenyl carbamate which is converted to ephedrine and pseudoephedrine is (1-benzoyl vinyl)-alkyl carbamate.

20. The method of claim 18 in which the urethane and carbonyl groups are reduced using lithium aluminum hydride or sodium borohydride as the reducing agent.

21. The method of claim 20 in which the assymmetric hydrogenation catalyst is a mixture of sodium borohydride and aluminum chloride.

* * * * *